United States Patent
Hansen et al.

(10) Patent No.: US 6,793,666 B2
(45) Date of Patent: Sep. 21, 2004

(54) DISTAL PROTECTION MECHANICALLY ATTACHED FILTER CARTRIDGE

(75) Inventors: James G. Hansen, Coon Rapids, MN (US); Gary L. Hendrickson, Big Lake, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 192 days.

(21) Appl. No.: 10/025,705

(22) Filed: Dec. 18, 2001

(65) Prior Publication Data

US 2003/0114880 A1 Jun. 19, 2003

(51) Int. Cl.[7] .............................................. A61M 29/00
(52) U.S. Cl. ...................................................... 606/200
(58) Field of Search ................................. 606/200, 127, 606/114, 159, 106; 604/104–106; 623/1.11

(56) References Cited

U.S. PATENT DOCUMENTS

| | | | |
|---|---|---|---|
| 438,980 A | * | 10/1890 | Barker |
| 1,828,986 A | * | 10/1931 | Stevens |
| 1,972,428 A | * | 9/1934 | Richard |
| 3,472,230 A | | 10/1969 | Fogarty |
| 3,952,747 A | | 4/1976 | Kimmell, Jr. |
| 3,996,938 A | | 12/1976 | Clark, III |
| 4,046,150 A | | 9/1977 | Schwartz et al. |
| 4,425,908 A | | 1/1984 | Simon |
| 4,590,938 A | | 5/1986 | Segura et al. |
| 4,619,246 A | | 10/1986 | Molgaard-Nielsen et al. |
| 4,650,466 A | | 3/1987 | Luther |
| 4,706,671 A | | 11/1987 | Weinrib |
| 4,723,549 A | | 2/1988 | Wholey et al. |
| 4,790,812 A | | 12/1988 | Hawkins, Jr. et al. |
| 4,790,813 A | | 12/1988 | Kensey |

(List continued on next page.)

FOREIGN PATENT DOCUMENTS

| | | |
|---|---|---|
| DE | 28 21 048 | 7/1980 |
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |

(List continued on next page.)

OTHER PUBLICATIONS

"Atherosclerotic Disease of the Aortic Arch as a Risk Factor of Recurrent Ischemic Stroke," The New England Journal of Medicine, pp. 1216–1221 (May 1996).
"Endovascular Grafts, Stents Drive Interventional Radiology Growth," *Cardiovascular Device Update*, 2(3):1–12 (Mar. 1996).
"Protruding Atheromas in the Thoracic Aortic and Systemic Embolization," pp. 423–427 American College of Physicians (1991).

(List continued on next page.)

*Primary Examiner*—Sharon Kennedy
(74) *Attorney, Agent, or Firm*—Crompton, Seager & Tufte LLC (57) ABSTRACT

Distal protection filter assembly and methods for coupling a filter to an elongate shaft. A filter assembly may include a tubular adaptor having a distal holding receptacle. The filter may include struts adapted and configured for being coupled to the holding receptacle.

21 Claims, 4 Drawing Sheets

U.S. PATENT DOCUMENTS

| | | |
|---|---|---|
| 4,794,928 A | 1/1989 | Kletschka |
| 4,807,626 A | 2/1989 | McGirr |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Gifford, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,110,190 A * | 5/1992 | Johnson |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,410 B1 | 5/2001 | Vrba et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 2001/0012951 A1 | 8/2001 | Bates et al. |
| 2002/0055767 A1 | 5/2002 | Forde et al. |

FOREIGN PATENT DOCUMENTS

| | | |
|---|---|---|
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 815 803 A1 | 7/1997 |
| EP | 0 852 132 A1 | 7/1998 |
| EP | 0 934 729 | 8/1999 |
| EP | 1 000 590 A1 | 11/1999 |
| EP | 1 157 673 A2 | 2/2001 |
| FR | 2 580 504 | 10/1986 |
| FR | 2 643 250 A1 | 8/1990 |
| FR | 2 666 980 | 3/1992 |
| FR | 2 694 687 | 8/1992 |

| | | |
|---|---|---|
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Recognition and Embolic Potential of Intraaortic Atherosclerotic Debris," American College of Cardiology (Jan. 1991).

Cragg, Andrew et al., "A New Percutaneous Vena Cava Filger," *AJR, 141*:601–604 (Sep. 1983).

Cragg, Andrew et al., "Nonsurgical Placement of Arterial Endoprosthesis: A New Technique Using Nitinol Wire," *AJR*, pp. 261–263 (Apr. 1983).

Diethrich et al., "Percutaneous Techniques for Endoluminal Carotid Interventions," *J. Endovasc. Surg., 3*:182–202 (1996).

Fadali, A. Moneim, "A filtering device for the prevention of particulate embolization during the course of cardiac surgery," *Surgery, 64*(3):634–639 (Sep. 1968).

Haissaguerre et al., "Spontaneous Initiation of Atrial Fibrillation by Ectopic Beats Originating in the Pulmonary Veins," *The New England Journal of Medicine, 339*(10):659–666 (Sep. 1988).

Jordan, Jr. et al., "Microemboli Detected by Transcranial Doppler Monitoring . . . ," *Cardiovascular Surgery, 7*(1)33–38 (Jan. 1999).

Lesh, "Can Catheter Ablation Cure Atrial Fibrillation?" *ACC Current Journal Review*, pp. 38–40 (Sep./Oct. 1997).

Lund et al., "Long–Term Patentcy of Ductus Arteriosus After Balloon Dilation: an Experimental Study," *Laboratory Investigation, 69*(4):772–774 (Apr. 1984).

Marache et al., "Percutaneous Transluminal Venous Angioplasty . . . ," *American Heart Jorunal, 125*(2 Pt 1):362–366 (Feb. 1993).

Mazur et al., "Directional Atherectomy with the Omnicath™: A Unique New Catheter System," *Catheterization and Cardiovascular Diagnosis, 31*:17–84 (1994).

Moussa, MD, Issaam "Stents Don't Require Systemic Anticoagulation . . . But the Technique (and Results) Must be Optimal," *Journal of Invasive Cardiol., 8*(E):3E–7E, (1996).

Nakanishi et al., "Catheter Intervention to Venous System Using Expandable Metallic Stents," *Rinsho Kyobu Geka, 14*(2):English Abstract Only (Apr. 1994).

Onal et al., "Primary Stenting for Complex Atherosclerotic Plaques in Aortic and Iliac Stenoses," *Cardiovascular & Interventional Radiology, 21*(5):386–392 (1998).

Theron et al., "New Triple Coaxial Catheter System for Carotid Angioplasty with Cerebral Protection," *American Journal of Neuroradiology, 11*:869–874 (1990).

Tunick et al., "Protruding atherosclerotic plaque in the aortic archo f patients with systemic embolization: A new finding seen by transesophageal echocardiography," *American Heart Journal 120*(3):658–660 (Sep. 1990).

Waksman et al., "Distal Embolization is Common After Directional Atherectomy . . . ," *American Heart Journal, 129*(3):430–435 (1995).

Wholey, Mark H. et al., PTA and Stents in the Treatment of Extracranial Circulation, *The Journal of Invasive Cardiology, 8*(E):25E–30E (1996).

* cited by examiner

DISTAL PROTECTION MECHANICALLY ATTACHED FILTER CARTRIDGE

BACKGROUND OF THE INVENTION

1. Field of the Invention

The present invention pertains to field of distal protection devices. More particularly, the present invention pertains to devices and methods for coupling a distal protection filter to an elongate shaft.

2. Description of the Related Art

Heart disease is a major problem in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature, both of which are highly undesirable. During angioplasty procedures, stenotic debris may also break loose due to manipulation of the blood vessel. Because of this debris, a number of devices, termed distal protection devices, have been developed to filter out this debris.

BRIEF SUMMARY OF THE INVENTION

The present invention pertains to adaptors for coupling devices to an elongate shaft. More particularly, the present invention pertains to adaptors for coupling a distal protection filter to a guidewire. In addition, the use of an adaptor in accordance with the present disclosure may allow a user to couple a distal protection filter to a number of different guidewires.

The adaptor may include a proximal end, a distal end, and a lumen adapted and configured to receive a guidewire. The adaptor may be coupled to the guidewire by a number of methods such as solder, bronze, adhesive or other technique. The adaptor may also be placed on the wire such that it can be slide along the wire to provide a floating filter. A holding receptacle may be disposed proximate of the distal end of the adaptor. The holding receptacle includes one or more grooves adapted to receive struts of a distal protection filter. In addition, a cap can be slidably disposed about the adaptor such that the cap can be disposed over the holding receptacle to substantially fix the struts in place and, thus, couple the filter to the guidewire.

DETAILED DESCRIPTION OF THE INVENTION

The following description should be read with reference to the drawings wherein like reference numerals indicate like elements throughout the several views. The detailed description and drawings illustrate example embodiments of the claimed invention.

Figure 1:
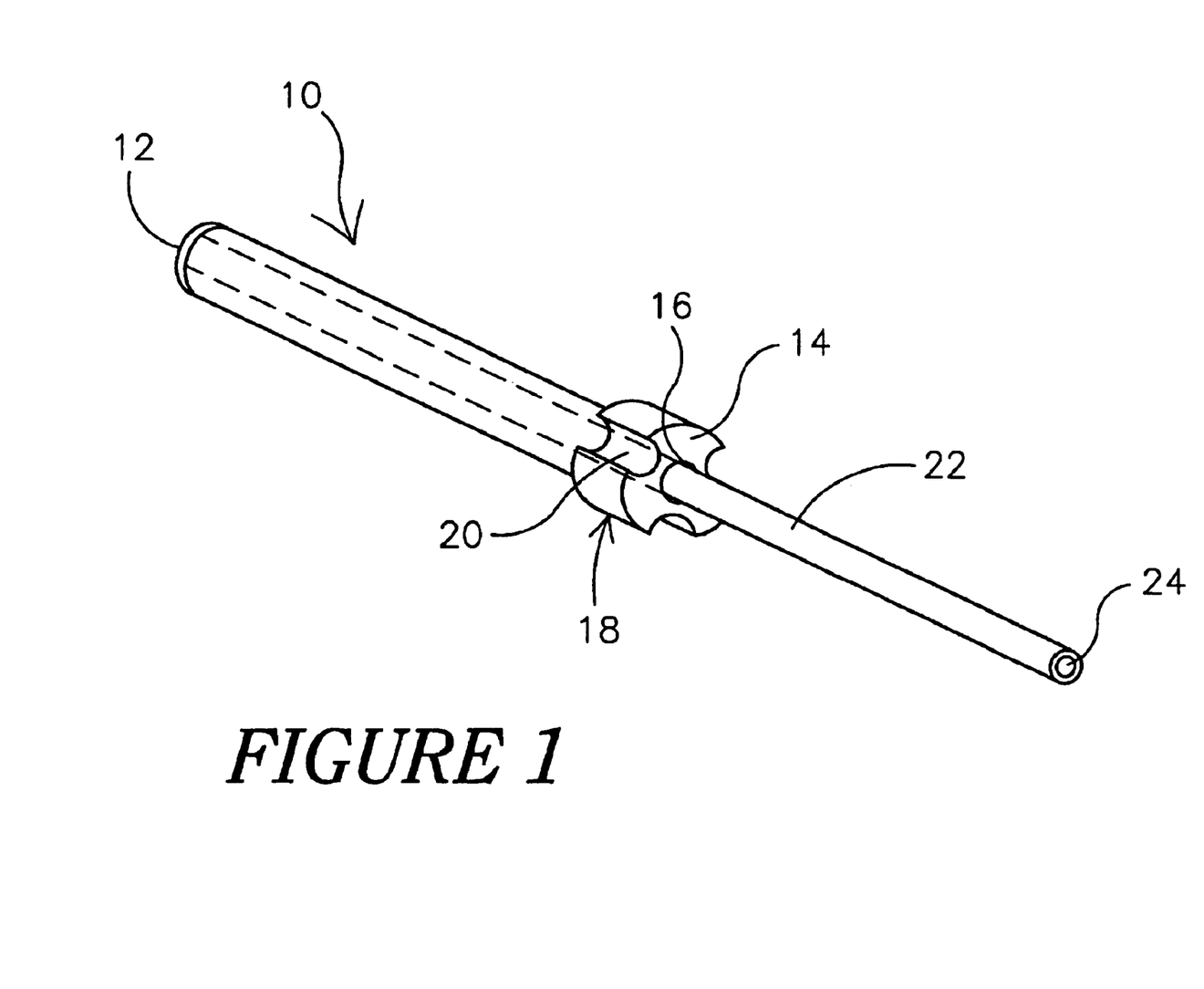
FIG. 1 is a perspective view of a tubular adaptor for coupling a distal protection filter to an elongate shaft.

FIG. 1 is a perspective view of a tubular adaptor 10 for coupling a distal protection filter to an elongate shaft. Adaptor 10 simplifies the process of coupling devices to a guidewire by permitting a user to couple a device to a number of different guidewires. Adaptor 10 may be generally cylindrical in shape and includes a proximal end 12, a distal end 14, and a lumen 16 extending therethrough. Lumen 16 can be adapted and configured for having an elongate shaft or guidewire disposed therein. Alternatively, the guidewire may be disposed within the lumen of a seal tube 22 as discussed below. Adaptor 10 may be comprised of a generally polymeric material, a metal or metal alloy, combinations thereof, or other suitable materials.

Whether the guidewire is disposed within lumen 16 or within the lumen of seal tube 22, adaptor 10 can be coupled to a guidewire by using one of several known techniques. For example, adaptor 10 may be crimped on the guidewire, soldered, brazed, laser or heat bonded, adhesively bonded, etc. If adaptor 10 is not fixedly attached to a wire or guidewire by adhesive or the like, adaptor 10 may be merely slidably and/or rotatably attached to the guidewire.

In order to accommodate a number of different guidewires, the inside diameter of lumen 16 may be sized to allow a particular guidewire to be disposed therein. For example, lumen 16 may having an inside diameter of about 0.005 to 0.020 inches or more. In addition, the overall profile of adaptor 10 should be sufficiently small to allow navigation through the vasculature of a patient, and may be sufficiently small enough to fit within the lumen of a guide catheter or other suitable device for delivery.

Adaptor 10 can include a holding receptacle 18. Holding receptacle 18 is generally cylindrical and includes one or more grooves 20 formed therein. Grooves 20 are adapted to receive at least a portion of a strut of a distal protection filter.

A seal tube 22 having an inner lumen 24 extending therethrough may be disposed within lumen 16. Seal tube 22 may be comprised of a thermoplastic elastomer such as Kraton® or other suitable materials that may substantially prevent fluid flow through lumen 16 (or inner lumen 24). Seal tube 22 may allow adaptor 10 to become substantially sealed to a guidewire, for example by friction fit. In addition, the inclusion of seal tube 22 may prevent fluid from passing through open portions of adaptor 10.

The size and length of seal tube 22 may be used to accommodate a number of wire or guidewires.

Figure 2:
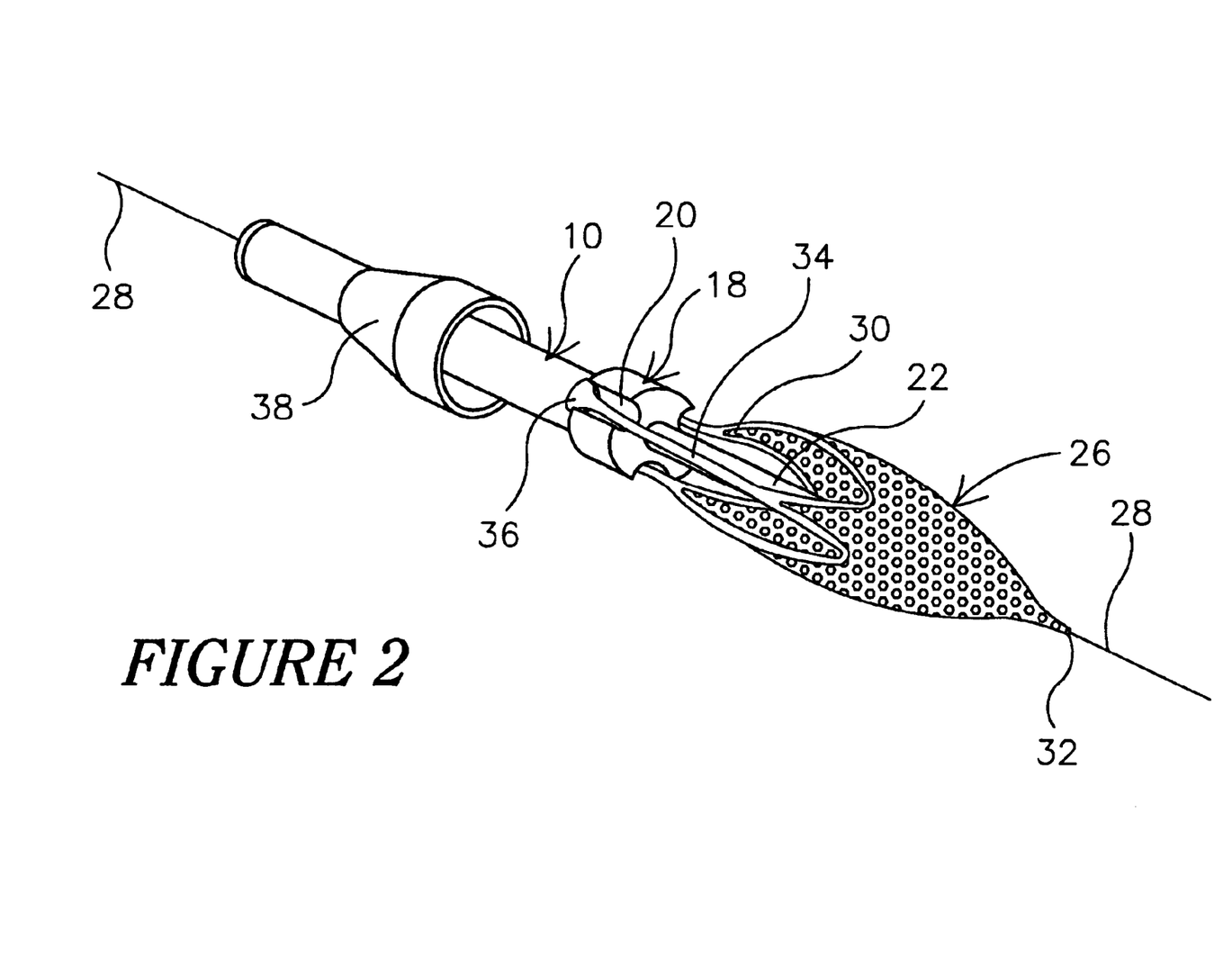
FIG. 2 is a perspective view of a tubular adaptor having a distal protection filter coupled thereto.

FIG. 2 is a perspective view of tubular adaptor 10 coupling a distal protection filter 26 to a guidewire 28. Filter 26 may be comprised of a polyurethane sheet disposed over a filter frame 27. The polyurethane sheet has at least one opening that may be, for example, formed by known laser techniques. The holes or openings are sized to allow blood flow therethrough but restrict flow of debris or emboli floating in the body lumen or cavity. Filter 26 may be generally cone-shaped, and have a proximal end 30 and a distal end 32. Distal end 32 may be a narrow, "V"—shaped end and proximal end 30 may have a relatively wide opening or mouth.

Filter 26 operates between a closed collapsed profile and an open radially-expanded deployed profile for collecting debris in a body lumen. In an expanded profile, the mouth is opened and the frame expands radially outwardly to support the mouth. A number of differing configurations of filter 26 may be substituted without departing from the spirit of the invention.

In addition, a portion of the filter frame 27 may include radiopaque materials. Radiopaque materials are understood to be capable of producing a relatively bright image on a fluoroscopy screen or another imaging technique during an intravascular procedure. This relatively bright image aids the user of distal protection assembly 10 in determining the location of filter 26. Radiopaque materials may include, but are not limited to, gold, platinum, tungsten alloy, and plastic material loaded with a radiopaque filler.

Filter frame 27 includes one or more struts 34. Struts 34 are adapted and configured to have at least a portion thereof disposed within grooves 20. In addition, struts 34 may include flared proximal ends 36 that may extend proximally of holding receptacle 18 when struts 34 are disposed within grooves 20. According to this embodiment, flared proximal ends 36 may serve to help hold struts 34 in grooves 20 and otherwise prevent distal movement of struts 34 (and, thus, movement of filter 26) relative to adaptor 10.

A cap 38 can be slidably disposed along the length of adaptor 10. Cap 38 may be generally conical and be adapted and configured to slide along adaptor 10 until cap 38 engages holding receptacle 18. Sliding cap 38 over holding receptacle 18 couples filter 26 to guidewire 28.

If adaptor 10 is placed on wire 28 as shown in FIG. 2, but is not fixedly attached thereto, it will be free to rotate and slide along the wire. This floating filter type design allows wire 28 to be rotated or translated without rotating or translating filter 26 when deployed in a body lumen.

Figure 3:
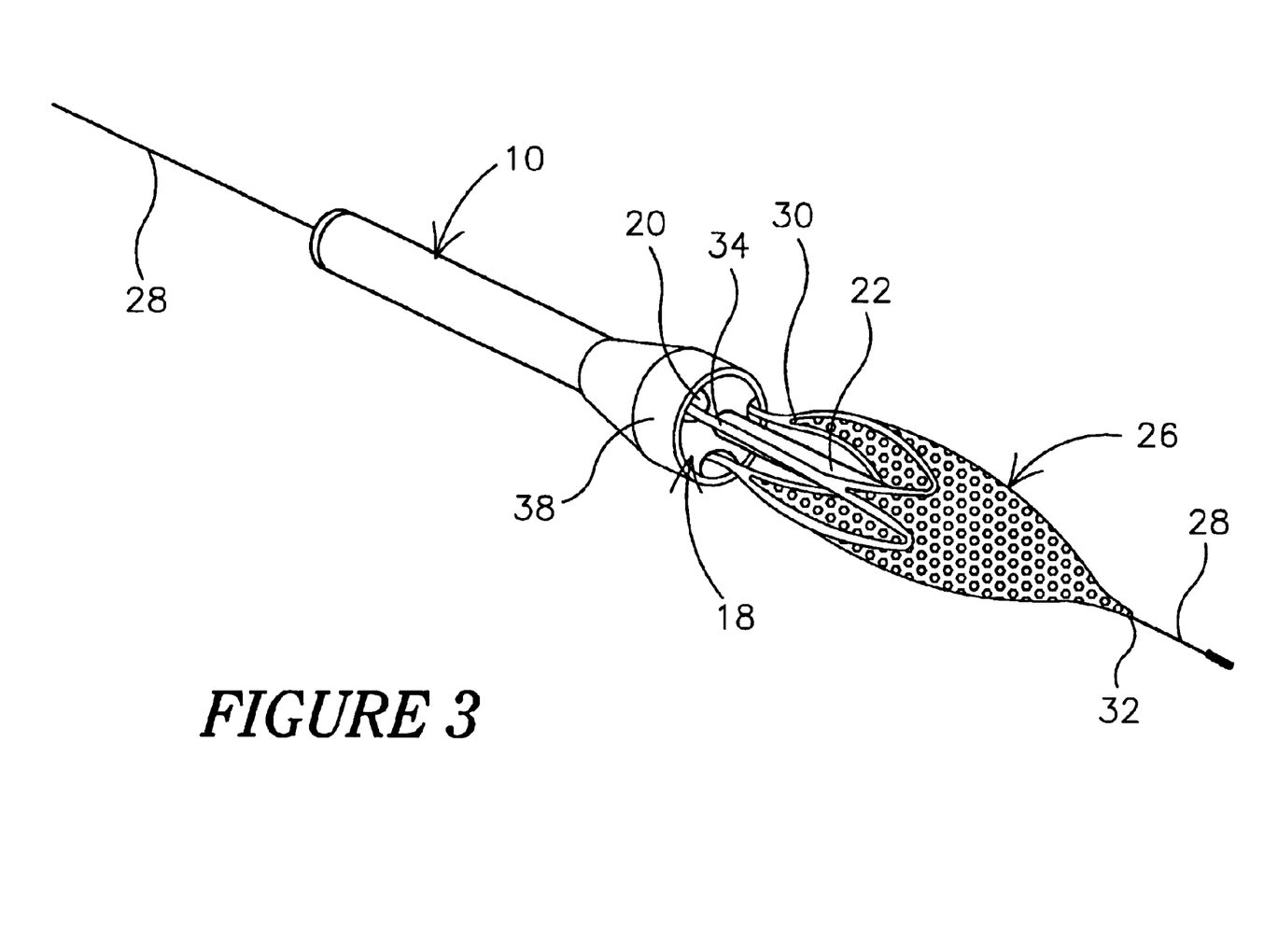
FIG. 3 is a perspective view of the tubular adaptor and filter in FIG. 2, wherein a cap is disposed over a portion of the struts.

FIG. 3 is a perspective view of tubular adaptor 10 and filter 26 wherein cap 38 is disposed over a portion of struts 34 to couple filter 26 to guidewire 28. When disposed over holding receptacle 18, cap 38 may be fixed in place, for example by adhesive. Alternatively, cap 38 may be fixed by crimping, laser or heat bonding, etc. In an exemplary embodiment, cap 38 may include a deflectable flange adapted to mate with a ring shank of holding receptacle 18. A number different methods may be used to fix cap 38 relative to holding receptacle 18 without departing from the spirit of the invention.

Having flared proximal ends 36 of struts 34 may help to securely couple filter 26 to guidewire 28. According to this embodiment, flared proximal ends 36 would substantially prevent struts 34 from being displaced from grooves 20. In an alternate embodiment, struts 34 may have a second set of flared surfaces spaced from ends 36 a distance greater than or equal to the length of channels defined by grooves 20. According to this embodiment, struts 34 may be fixed within grooves 20 by multiple sets of flares on opposite ends of grooves 20. Moreover, grooves 20 may include one or more depressions and struts 34 may include an equal number of projections. According to this embodiment, the projections and the depression would be designed to mate and, thus, couple filter 26 to guidewire 28.

Figure 4:
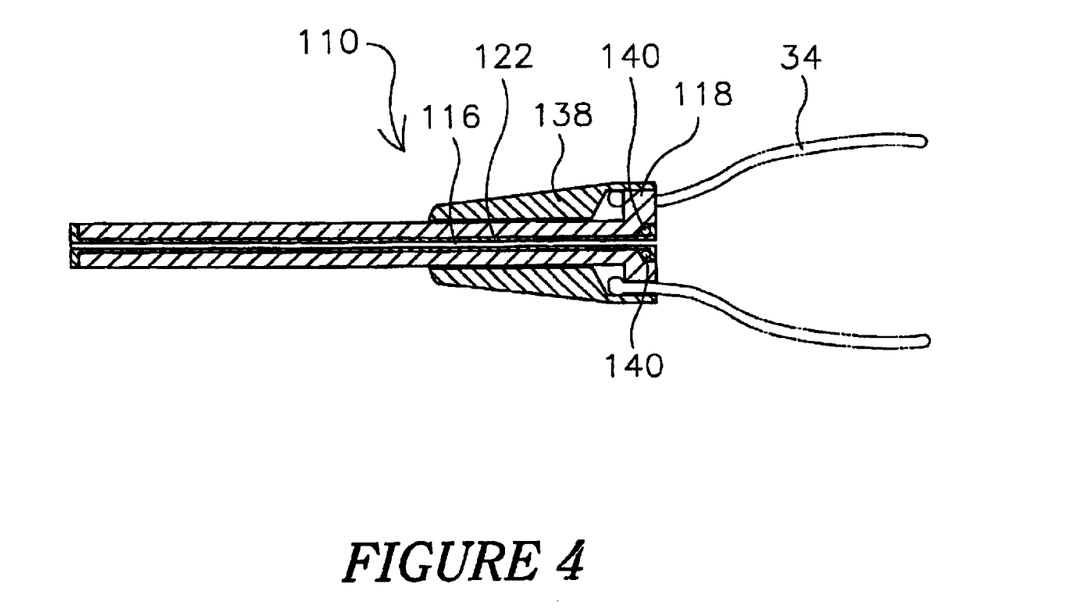
FIG. 4 is a partial cross sectional view of an alternate adaptor for coupling a distal protection filter to an elongate shaft.

FIG. 4 is a partial cross-sectional view of an alternate adaptor 110 that is essentially the same in form and function as adaptor 10 but further including one or more bearings 140 disposed proximate seal tube 122. More particularly, bearings 140 may be disposed near where holding receptacle 118 and cap 138 couple struts 34 to adaptor 110. Bearings 140 allow adaptor 110 to rotate (along with filter 26) about seal tube 122. Analogously, bearings 140 may allow guidewire 28 and seal tube 122 (i.e., when guidewire 28 and seal tube 122 are coupled) to rotate within adaptor 110 without altering the position of filter 26.

Seal tube 122 is essentially the same as seal tube 22 described above and includes lumen 116. The embodiment illustrated in FIG. 4 also shows seal tube 122 as being truncated at holding receptacle 118 (as opposed to seal tube 22 shown in FIGS. 1–3). It can be appreciated that the truncated version of seal tube 122 is equally applicable the embodiments shown in FIGS. 1–3 and that the elongated seal tube 22 of FIGS. 1–3 could be used in FIG. 4.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A distal protection filter assembly, comprising:
   an adaptor having a proximal end, a distal end, and a lumen extending therethrough, the adaptor including a holding receptacle having a plurality of slots;
   a distal protection filter having a plurality of struts;
   wherein the plurality of struts are coupled to and retained within the plurality of slots of the holding receptacle;
   further comprising a seal tube disposed within the lumen of the adaptor, the seal tube having a proximal end, a distal end, and a lumen extending therethrough; and
   further comprising one or more bearings disposed proximate the seal tube and the holding receptacle, the bearings adapted and configured to permit rotation of the seal tube relative to the adaptor.

2. A method of coupling a distal protection filter to a guidewire, comprising the steps of:
   providing a guidewire;
   providing a tubular adaptor having a proximal end, a distal end, a lumen extending therethrough, and a cap slidably disposed thereabout, wherein the distal end includes a holding receptacle;
   disposing the guidewire within the lumen,
   coupling the tubular adaptor to the guidewire;
   providing a distal protection filter having a plurality of struts;
   coupling the struts to the holding receptacle; and
   sliding the cap over the struts.

3. The method in accordance with claim 2, wherein the tubular adaptor further comprises a seal tube and wherein the stop of disposing the guidewire within the lumen includes disposing the guidewire within a lumen of the seal tube.

4. The method in accordance with claim 2, wherein the step of coupling the tubular adaptor to the guidewire includes soldering the tubular adaptor to the guidewire.

5. The method in accordance with claim 2, wherein the step of coupling the tubular adaptor to the guidewire includes crimping the tubular adaptor onto the guidewire.

6. The method in accordance with claim 2, wherein the step of coupling the tubular adaptor to the guidewire includes adhesively bonding the adaptor to the guidewire.

7. The method in accordance with claim 2, wherein the step of coupling the tubular adaptor to the guidewire includes thermal bonding the adaptor to the guidewire.

8. The method in accordance with claim 2, wherein the holding receptor includes one or more grooves, and wherein the step of coupling the filter to the holding receptacle includes disposing the struts within the grooves.

9. The method in accordance with claim 2 wherein the struts have flared proximal ends, and wherein the step of coupling the filter to the holding receptacle includes disposing the flared proximal end proximal to the holding receptacle.

10. The method in accordance with claim 2, further comprising the step of fixedly coupling the cap to the tubular adaptor.

11. The method in accordance with claim 10, wherein the step of fixedly coupling the cap to the tubular adaptor includes adhesive bonding.

12. A method of coupling a distal protection filter to a guidewire, comprising the steps of:

providing an elongate shaft;

providing a mechanical attachment having a proximal end, a distal end, a lumen extending therethrough, and a cap slidably disposed thereabout, wherein the distal end includes a holding receptacle having one or more grooves;

disposing the shaft within the lumen, coupling the mechanical attachment to the shaft;

providing a distal protection filter having a plurality of struts;

disposing the struts within the grooves; and sliding the cap over the struts.

13. The method in accordance with claim 12, wherein the mechanical attachment further comprises a seal tube and wherein the step of disposing the shaft within the lumen includes disposing the shaft within a lumen of the seal tube.

14. The method in accordance with claim 12, wherein the step of coupling the mechanical attachment to the shaft includes soldering the mechanical attachment to the shaft.

15. The method in accordance with claim 12, wherein the step of coupling the mechanical attachment to the shaft includes crimping the mechanical attachment onto the shaft.

16. The method in accordance with claim 12, wherein the step of coupling the mechanical attachment to the shaft includes adhesively bonding the mechanical attachment to the shaft.

17. The method in accordance with claim 12, wherein the step of coupling the mechanical attachment to the shaft includes thermal bonding the mechanical attachment to the shalt.

18. The method in accordance with claim 12, wherein the struts have flared proximal ends, and wherein the step of coupling the filter to the holding receptacle includes disposing the flared proximal end proximal to the holding receptacle.

19. The method in accordance with claim 12, further comprising the step of fixedly coupling the cap to the mechanical attachment.

20. The method in accordance with claim 19, wherein the step of fixedly coupling the cap to the tubular adaptor includes adhesive bonding.

21. A distal protection filter assembly, comprising:

an adaptor having a proximal end, a distal end, and a lumen extending therethrough;

a seal tube disposed within the lumen of the adaptor;

wherein the distal end of the adaptor includes a holding receptacle;

one or more bearings disposed between the seal tube and the holding receptacle, the bearings adapted and configured to permit rotation of the seal tube relative to the adaptor;

a cap disposed about the holding receptacle;

a distal protection filter having a plurality of struts, the struts being coupled to the holding receptacle.

* * * * *

UNITED STATES PATENT AND TRADEMARK OFFICE
CERTIFICATE OF CORRECTION

PATENT NO. : 6,793,666 B2 Page 1 of 1
DATED : September 21, 2004
INVENTOR(S) : James G. Hansen and Gary L. Hendrickson It is certified that error appears in the above-identified patent and that said Letters Patent is hereby corrected as shown below:

Column 4,
Line 59, delete "stop" and insert -- step --

Column 6,
Line 14, delete "shalt" and insert "shaft"

Signed and Sealed this

Twenty-second Day of February, 2005

JON W. DUDAS
*Director of the United States Patent and Trademark Office*